(12) United States Patent
Huang et al.

(10) Patent No.: US 11,319,570 B2
(45) Date of Patent: *May 3, 2022

(54) MICRO BIOSENSOR AND MEASURING METHOD THEREOF

(71) Applicant: BIONIME CORPORATION, Taichung (TW)

(72) Inventors: Chun-Mu Huang, Taichung (TW); Chieh-Hsing Chen, Taichung (TW)

(73) Assignee: BIONIME CORPORATION, Taichung (TW)

( * ) Notice: Subject to any disclaimer, the term of this patent is extended or adjusted under 35 U.S.C. 154(b) by 0 days.

This patent is subject to a terminal disclaimer.

(21) Appl. No.: 16/945,292

(22) Filed: Jul. 31, 2020

(65) Prior Publication Data

US 2021/0030329 A1 Feb. 4, 2021

Related U.S. Application Data

(60) Provisional application No. 62/988,549, filed on Mar. 12, 2020, provisional application No. 62/882,162, filed on Aug. 2, 2019.

(51) Int. Cl.
*A61B 5/145* (2006.01)
*A61B 5/1486* (2006.01)
(Continued)

(52) U.S. Cl.
CPC .......... *C12Q 1/002* (2013.01); *A61B 5/1473* (2013.01); *A61B 5/14503* (2013.01);
(Continued)

(58) Field of Classification Search
CPC .......... A61B 5/14532; A61B 5/14546; A61B 5/1473–14735; A61B 5/1451;
(Continued)

(56) References Cited

U.S. PATENT DOCUMENTS 6,002,954 A * 12/1999 Van Antwerp ..... A61B 5/14532
600/310
2009/0294306 A1 12/2009 Feldman et al.
(Continued)

FOREIGN PATENT DOCUMENTS

WO 2016202722 A1 12/2016
WO WO-2018187237 A1 * 10/2018 ........... A61N 1/0551
WO WO-2019004585 A1 * 1/2019 ............ A61B 5/145

OTHER PUBLICATIONS

Machine Translation of WO 2019/004585 (Year: 2021).*
EPO, Extended European Search Report for European Patent Application No. 20189167.8, dated Nov. 27, 2020. 11 pages.

*Primary Examiner* — Eric F Winakur
*Assistant Examiner* — Alice Ling Zou
(74) *Attorney, Agent, or Firm* — Perkins Coie LLP; Viola Kung

(57) ABSTRACT

The present invention provides a measuring method for prolonging a usage lifetime of a micro biosensor implanted subcutaneously to measure a physiological signal associated with an analyte. The micro biosensor includes a working electrode and a counter electrode, wherein the counter electrode includes silver and a silver halide having an initial amount. The method includes cyclic steps of: applying a measurement voltage to drive the working electrode to measure the physiological signal, where the silver halide is consumed by a specific amount; stopping applying the measurement voltage; and whenever the physiological parameter is obtained, applying a replenishment voltage to drive the counter electrode, thereby the silver halide of a replenishment amount being replenished to the counter electrode, wherein a guarding value of a sum of the replenishment amount and the initial amount subtracting the consumption amount is controlled within a range of the initial amount plus or minus a specific value.

20 Claims, 13 Drawing Sheets

(51) Int. Cl.
*C12Q 1/00* (2006.01)
*G01N 27/327* (2006.01)
*A61B 5/1473* (2006.01)
*G01N 27/49* (2006.01)

(52) U.S. Cl.
CPC ...... *A61B 5/14532* (2013.01); *A61B 5/14546* (2013.01); *A61B 5/14735* (2013.01); *A61B 5/14865* (2013.01); *C12Q 1/005* (2013.01); *G01N 27/3271* (2013.01); *G01N 27/3273* (2013.01); *G01N 27/49* (2013.01); *A61B 2560/0468* (2013.01); *A61B 2562/028* (2013.01); *A61B 2562/0215* (2017.08); *A61B 2562/125* (2013.01); *A61B 2562/16* (2013.01)

(58) Field of Classification Search
CPC .............. A61B 5/1486; A61B 5/14503; A61B 5/14865; A61B 2562/028; A61B 2562/0295
See application file for complete search history.

(56) References Cited

U.S. PATENT DOCUMENTS

| 2009/0298104 | A1 | 12/2009 | Liu et al. |
| 2011/0259741 | A1 | 10/2011 | Murase et al. |
| 2013/0245412 | A1 | 9/2013 | Rong et al. |
| 2018/0100826 | A1* | 4/2018 | Marquant ............ G01N 27/301 |

* cited by examiner

MICRO BIOSENSOR AND MEASURING METHOD THEREOF

CROSS-REFERENCE TO RELATED APPLICATION AND CLAIM OF PRIORITY

This application claims the benefit of the U.S. Provisional Patent Application No. 62/882,162, filed on Aug. 2, 2019, and the U.S. Provisional Patent Application No. 62/988,549, filed on Mar. 12, 2020 at the U.S. Patent and Trademark Office, the disclosures of which are incorporated herein in their entirety by reference.

FIELD OF THE INVENTION

The present invention is related to a micro biosensor and a measuring method thereof. Particularly, the present invention is related to a micro biosensor and a measuring method thereof for prolonging a usage lifetime of the micro biosensor.

BACKGROUND OF THE INVENTION

The population of diabetic patients is growing rapidly, and there is increasing emphasis on the need to monitor glucose changes in the human body. Therefore, many studies have begun to develop a system that can be implanted in the human body for continuous glucose monitoring (CGM) system to solve the inconvenience to the patient resulting from the repeated blood samplings and detections performed each day.

In the field of an enzyme-based biosensor of CGM system in which a biochemical reaction signal that depends on the concentration of an analyte is converted into a measurable physical signal, such as an optical or electrochemical signal. In case of a measurement of glucose, the electrochemical reaction occurs so that the glucose oxidase (GOx) catalyzes the glucose to react and produce the gluconolactone and the reduced enzyme. Then, the reduced enzyme transfers electrons to the oxygen in the biofluid in the living body to produce a product hydrogen peroxide ($H_2O_2$), and the concentration of the glucose is quantified by oxidizing the product $H_2O_2$. The reaction is as follows:

Glucose+GOx (FAD)→GOx(FADH$_2$)+Gluconolactone

GOx(FADH$_2$)+O$_2$→GOx(FAD)+H$_2$O$_2$

wherein the FAD (which is Flavin Adenine Dinucleotide) is an active center of the GOx.

A user usually wears the CGM system for a long period of time, for example at least 14 days, thus the miniaturization of its size is a necessary development. The basic structure of a CGM system comprises: (a) a biosensor, which measures the physiological signals corresponding to the glucose concentration in the human body; and (b) a transmitter for transmitting these physiological signals. The biosensor may be a two-electrode system or a three-electrode system. The biosensor with a three-electrode system includes a working electrode (WE), a counter electrode (CE), and a reference electrode (RE). The biosensor with a two-electrode system includes a working electrode (WE) and a counter electrode (CE), in which the counter electrode also functions as a reference electrode, and is sometimes called a counter/reference electrode (R/C) accordingly. For the reference electrode in the biosensor with the three-electrode system and for the counter electrode also functioning as a reference electrode in the biosensor with the two-electrode system, a suitable material applicable for a stable measurement to the concentration of the glucose is silver and silver chloride (Ag/AgCl). However, after the biosensor is implanted into a living body, when an oxidation-reaction occurs on the working electrode to measure the concentration of the glucose, a reduction reaction occurs on the corresponding reference electrode (R) or reference/counter electrode (R/C) to cause the AgCl to be reduced to Ag and the AgCl is consumed. In addition, if the biosensor implanted into the living body is a biosensor with the two or three-electrode system, the depletion of the silver chloride from the reference electrode will occur due to its dissolution in the body fluid, and will cause a drifting problem to the reference voltage. However, due to the reaction of the reference/counter electrode (R/C) of the two-electrode system, the consumption of silver chloride is even higher than that of the three-electrode system. Therefore, the usage lifetime of the biosensor is limited by the content of the silver chloride on the counter electrode and/or the reference electrode.

There are also many inventions proposed to address this problem. Taking a biosensor with a two-electrode system as an example, the consumption on the counter electrode is about 1.73 millicoulombs (mC) per day at an average sensing current of 20 nanoamperes (nA). Assuming that the length, width and height of the counter electrode are 3.3 mm, 0.25 mm and 0.01 mm respectively and the originally designed electrode capacity is only 6 mC, the stable measurement that the biosensor can provide can be maintained for about one day at most. However, if it is necessary to further prolong the usage lifetime of the biosensor so that the subcutaneously implanted biosensor can support continuous glucose monitoring for 16 days, the capacity of the counter electrode must be at least 27.68 mC. Without changing the width and thickness of the counter electrode, the length of the counter electrode in the prior art needs to be up to 15.2 mm. Accordingly, the length of the counter electrode of the biosensor has been extended to be larger than 10 mm in the prior art. However, in order to avoid such a kind of biosensor being implanted deeply into the subcutaneous tissues, the biosensor needs to be implanted at an oblique angle. Therefore, it causes problems such as a larger implantation wound and a higher risk of infection to the patient, and because the implantation length is long, the pain during implantation is also more significant.

U.S. Pat. No. 8,620,398 describes a biosensor, which is mainly with a three-electrode system. Although the reference electrode basically does not participate in the chemical reaction, the silver chloride is still gradually consumed naturally in the environment in vivo, the consumption rate is slower than that in the counter electrode of the two-electrode system. The specification disclosed that the AgCl regenerates when the AgCl is almost totally consumed. That is to say, until the measured signals are unstable, or until the measured signals are all noises, the replenishment process will be activated to recover the AgCl back to having the amount sufficient to perform a plurality of measurements. Then, until next time when the noise occurs again, AgCl needs to be replenished again. It can be understood that, although U.S. Pat. No. 8,620,398 considers that AgCl will be consumed in the measurement and replenishing AgCl when the biosensor fails, the measured value at the time of failure can no longer be trusted. It is necessary to wait for the biosensor to complete the AgCl replenishment procedure so as to obtain the correct measured value, to temporarily perform the measurement by taking a blood sample, or to skip this measurement directly. This problem is always troublesome for the patient or those who need to know the present concentration of the blood glucose. In addition, because the biosensor has to deal with a plurality of measurements of consecutive several measurements or over several days, more AgCl capacity must be prepared. However, it will inevitably result in the problem of a longer implantation length of the biosensor. U.S. Pat. No. 8,620, 398 has not proposed anything about the timely AgCl replenishment method that can provide uninterrupted measurements, and a shorter implantation length and a longer usage lifetime of the biosensor.

U.S. Pat. No. 9,351,677 proposes a sensor to measure an analyte, which is mainly with a two-electrode system, The reference/counter electrode (R/C) participates in the chemical reaction, so the silver chloride is consumed by the electrochemical reaction. The patent disclosed an analyte sensor with an increased AgCl capacity. The sensor uses $H_2O_2$ to regenerate AgCl on the reference electrode. However, because $H_2O_2$ is easily reduced to $H_2O$ or oxidized to $O_2$, it is not easy to be stably present in the human body. Therefore, during the regeneration/replenishment period, the concentration of $H_2O_2$ in the human body may not be enough to stably replenish a sufficient amount of AgCl, and the biosensor needs to be equipped with a larger AgCl electrode size, and the implantation end is also up to 12 mm long.

Therefore, the present disclosure provides a biosensor, which is capable of achieving the effects of providing uninterrupted measurements by replenishing AgCl after measuring, stably replenishing AgCl, prolonging the usage lifetime of the biosensor, and miniaturizing the implantation end of the biosensor to a compact size, and reducing the manufacturing cost of the product. These effects can solve the aforementioned problems that the prior art has found impossible to overcome.

In view of the above, because of the defect in the prior art, the inventors provide the present invention to effectively overcome the disadvantages of the prior art. The descriptions of the present invention are as follows:

SUMMARY OF THE INVENTION

By the replenishing technique in the present invention, the micro biosensors in the present invention have a prolonged usage lifetime and the size of the signal sensing section of the counter electrode in the micro biosensor can be reduced, which can reduce biological toxicity. In addition, the reduced size of the electrode specifically refers to the shortened length of the implantation end of the sensor, which would reduce pain for the user during implantation.

In accordance with another aspect of the present disclosure, a method of measuring an analyte using a biosensor for prolonging a usage lifetime of the biosensor implanted subcutaneously to measure a physiological signal representative of a physiological parameter associated with the analyte in a biofluid is disclosed. The biosensor includes a working electrode and a counter electrode, the working electrode is at least partially covered by a chemical reagent configured to react with the analyte, and the counter electrode has silver and a silver chloride. The method includes the following cyclic steps of: a) performing a measurement step, including sub-steps of: i. applying a measurement potential difference across the working electrode and the counter electrode so that the working electrode has a higher voltage than that of the counter electrode during a measurement period, causing a first oxidation reaction to occur on the working electrode having an electrochemical reaction with the chemical reagent and the analyte, thereby the working electrode outputs a physiological signal, where the silver halide of the counter electrode has a consumption amount corresponding to the physiological signal; and ii. removing the measurement potential difference to stop the physiological signal measurement step, and converting the physiological signal to output a physiological parameter; and b) performing a replenishment step, including sub-steps of: i. applying a replenishment potential difference across the counter electrode and the working electrode during a replenishment period so that the counter electrode has a higher voltage than that of the working electrode, causing a second oxidation reaction to occur to the silver on the counter electrode, so that the silver chloride gains a replenishment amount, wherein the replenishment amount is related to the consumption amount that the silver halide of the counter electrode has an amount maintained in a safe storage range, and a next physiological signal and a next physiological parameter obtained in a next measurement step are kept in a stable correlation; and ii. removing the replenishment potential difference to stop the replenishment step.

In accordance with one more aspect of the present disclosure, a method of measuring an analyte using a biosensor for prolonging a usage lifetime of the biosensor implanted subcutaneously to measure a physiological signal representative of a physiological parameter associated with the analyte in a biofluid is disclosed. The biosensor includes a working electrode and a counter electrode, the working electrode is at least partially covered by a chemical reagent, and the counter electrode includes silver and a silver halide having an initial amount. The method comprising cyclic steps of: applying a measurement voltage to drive the working electrode to measure the physiological signal, thereby obtaining the physiological parameter, where the silver halide is consumed by a specific amount; stopping applying the measurement voltage; and whenever the physiological parameter is obtained, applying a replenishment voltage to drive the counter electrode to cause an oxidation reaction, thereby the silver halide of a replenishment amount being replenished to the counter electrode, wherein a guarding value of a sum of the replenishment amount and the initial amount subtracting the consumption amount is controlled within a range of the initial amount plus or minus a specific value.

In accordance with one more aspect of the present disclosure, a micro biosensor for implanting subcutaneous implantation to measure a physiological parameter representative of a physiological signal associated with an analyte in a living body is provided. The micro biosensor includes: a substrate; a chemical reagent; a working electrode disposed on the substrate, at least partially covered by the chemical reagent, and driven for a first oxidation reaction to measure the physiological signal for obtaining the physiological parameter within a measurement period; a counter electrode disposed on the substrate, and including a silver and a silver halide having an initial amount and being consumed in a specific amount within the measurement period; and whenever the respective physiological parameter is obtained, driving the counter electrode for a second oxidation reaction within a replenishment period, thereby the silver halide of a replenishment amount being replenished to the counter electrode, wherein a guarding value of a sum of the replenishment amount and the initial amount subtracting the consumption amount is controlled within a range of the original amount plus or minus a specific value.

BRIEF DESCRIPTION OF THE DRAWINGS

The above embodiments and advantages of the present invention will become more readily apparent to those ordinarily skilled in the art after reviewing the following detailed descriptions and accompanying drawings.

DETAILED DESCRIPTION OF THE PREFERRED EMBODIMENTS

Please refer to all figures of the present invention when reading the following detailed description, wherein all Figures of the present invention demonstrate different embodiments of the present invention by showing examples, and help the skilled person in the art to understand how to implement the present invention. The present examples provide sufficient embodiments to demonstrate the spirit of the present invention, each embodiment does not conflict with the others, and new embodiments can be implemented through an arbitrary combination thereof, i.e., the present invention is not restricted to the embodiments disclosed in the present specification.

Unless there are other restrictions defined in the specific example, the following definitions apply to the terms used throughout the specification.

The term "amount" refers to a capacity of silver halide (AgX) or silver chloride (AgCl) on the counter electrode, and preferably represents in a unit of micro Coulomb ($\mu C$), milli Coulomb (mC) or Coulomb (C), but is not limited to concentration by weight percentage (wt %), mole number, molar concentration, etc.

Figure 1:
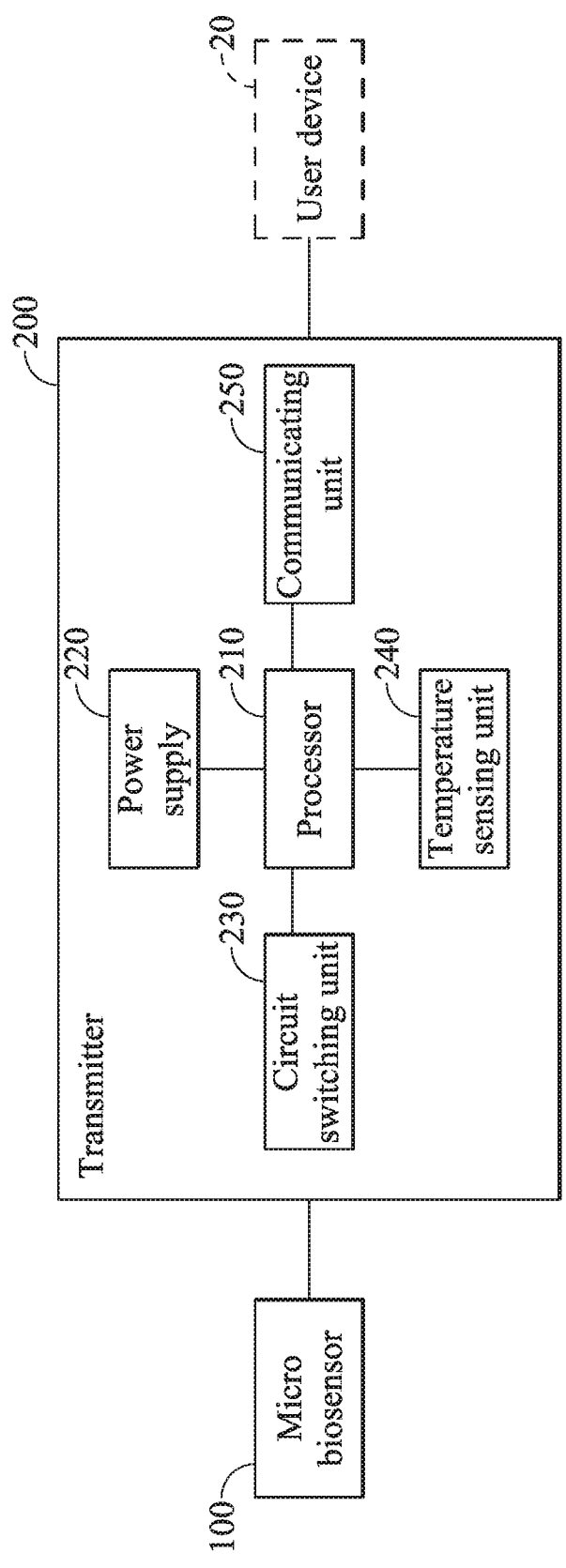
FIG. 1 shows a schematic diagram of a physiological signal measurement device of the present invention.

Please refer to FIG. 1, which is a schematic diagram of a physiological signal measurement device of the present invention. The physiological signal measurement device 10 of the present invention can be implanted subcutaneously to measure a physiological signal representing a physiological parameter associated with an analyte in a biofluid. The physiological signal measurement device 10 of the present invention includes a micro biosensor 100 and a transmitter 200, wherein the transmitter 200 is electrically connected to the micro biosensor 100 and includes a processor 210, a power supply 220, a circuit switching unit 230, a temperature sensing unit 240 and a communicating unit 250. The power supply 220 provides a voltage to the micro biosensor 100 through the circuit switching unit 230 for measuring the physiological signal, the temperature sensing unit 240 measures the body temperature of the living body, thereby the temperature measuring signal and the measured physiological signal measured by the micro biosensor 100 are transmitted to the processor 210, and the processor 210 operates the measured physiological signal to a physiological parameter. The communicating unit 250 can communicate with a user device 20 by a wire or wireless transmission.

Figure 2A:
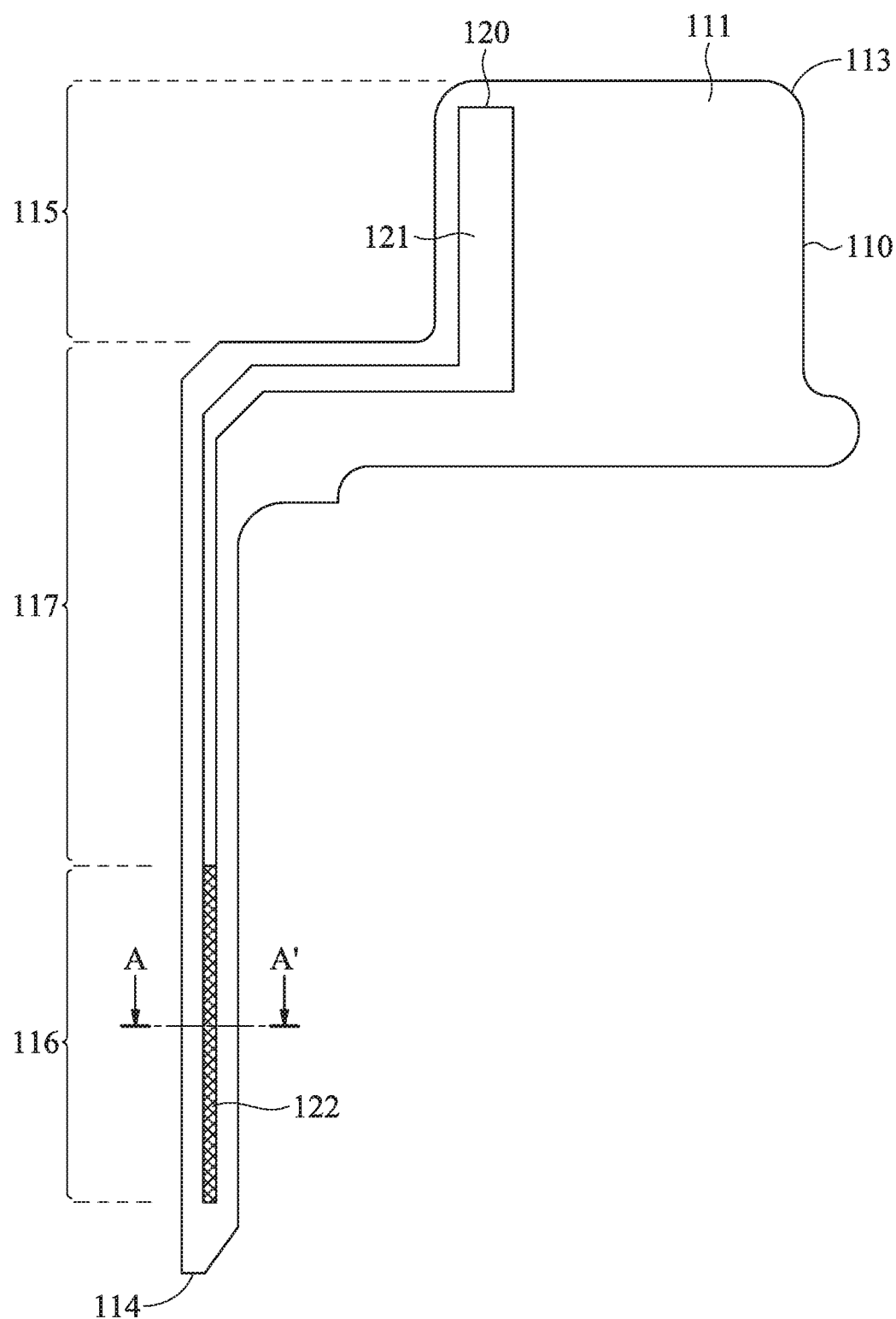
FIG. 2A shows a front schematic diagram of a micro biosensor of the present invention.
Figure 2B:
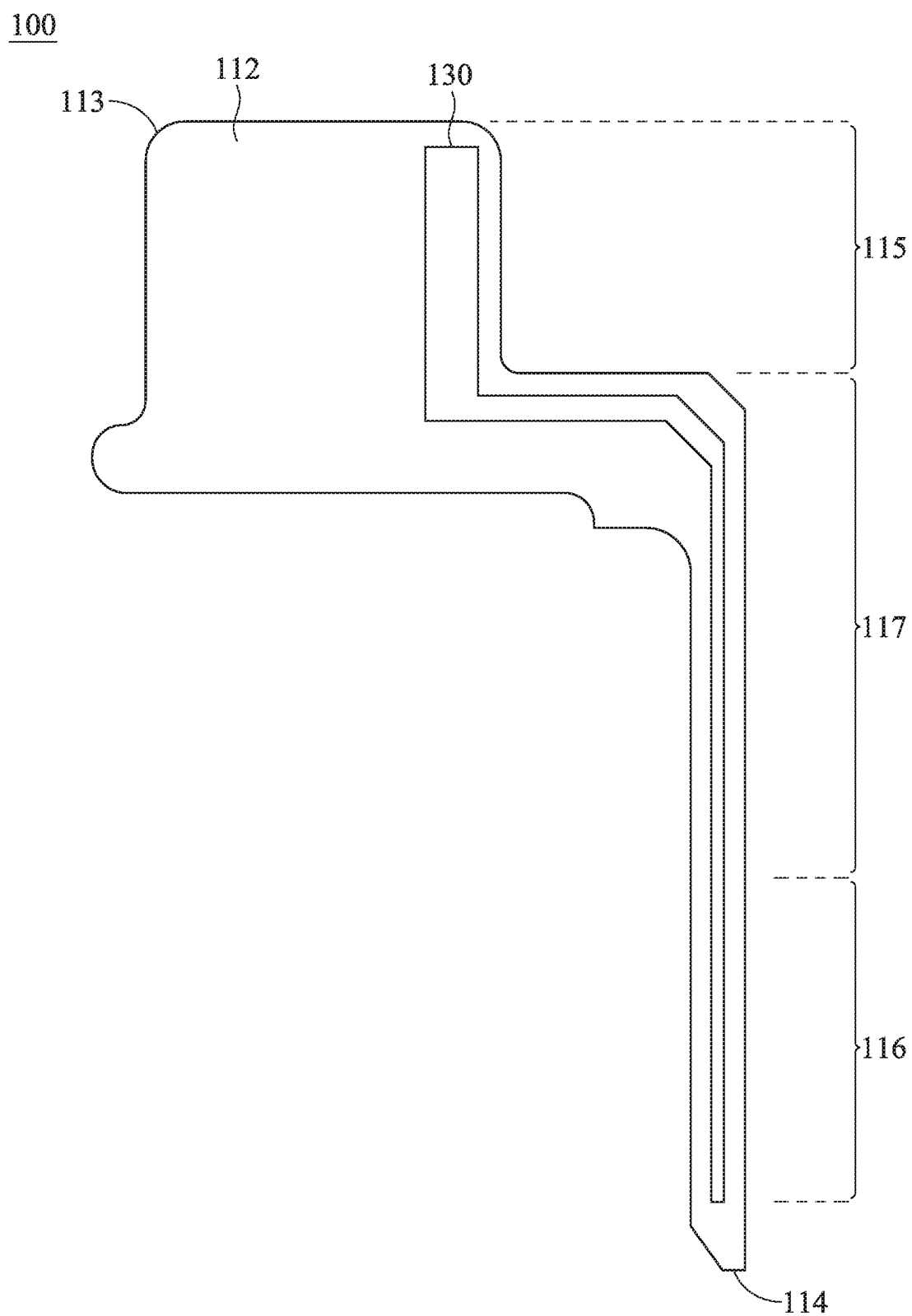
FIG. 2B shows a back schematic diagram of a micro biosensor of the present invention.
Figure 2C:
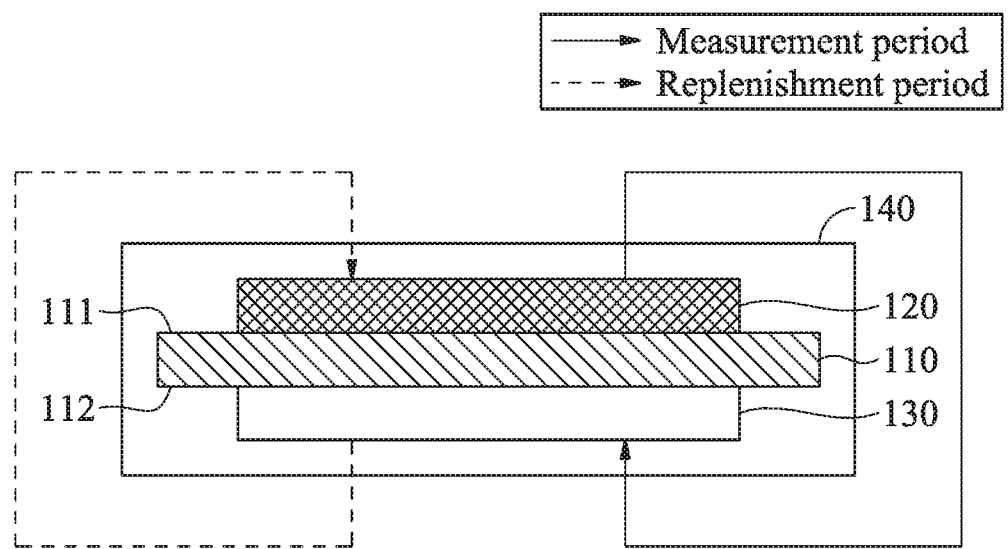
FIG. 2C shows a sectional schematic diagram of a cut view of the micro biosensor along the section line A-A' in FIG. 2A.

Please refer to FIGS. 2A and 2B, which are front and back schematic diagrams of the micro biosensor of the present invention. The micro biosensor 100 of the present invention includes a substrate 110, a working electrode 120 and a counter electrode 130 disposed on the substrate 110, and a chemical reagent 140 (as shown in FIG. 2C) covering the working electrode 120 and the counter electrode 130. The material of the substrate 110 can be any material that is known to be suitable for use in electrode substrates and preferably has flexibility and insulation properties, such as but not limited to: polymer materials such as polyester and polyimide. The aforementioned polymer materials can be used alone or in combination. The substrate 110 includes a surface 111 (i.e. a first surface), an opposite surface 112 (i.e. a second surface) opposite to the surface 111, a first end 113 and a second end 114. The substrate 110 is separated into three areas respectively—they are a signal output area 115 located close to the first end 113, a sensing area 116 located close to the second end 114, and a connecting area 117 located between the signal output area 115 and the sensing area 116. The working electrode 120 is disposed on the surface 111 of the substrate 110 and extended from the first end 113 to the second end 114 of the substrate 110. The working electrode 120 includes a signal output section 121 located in the signal output area 115 of the substrate 110, and a signal sensing section 122 located in the sensing area 116 of the substrate 110. A material of the working electrode 120 includes but is not limited to: carbon, platinum, aluminum, gallium, gold, indium, iridium, iron, lead, magnesium, nickel, manganese, molybdenum, osmium, palladium, rhodium, silver, tin, titanium, zinc, silicon, zirconium, a mixture thereof, or derivatives thereof (such as alloys, oxides or metal compounds, etc.). Preferably, the material of the working electrode 120 is a precious metal, a precious metal derivative or a combination thereof. More preferably, the working electrode 120 is made of platinum-containing material.

The counter electrode 130 is disposed on the opposite surface 112 of the substrate 110 and extended from the first end 113 to the second end 114 of the substrate 110. The counter electrode 130 includes a signal output section 131 located in the signal output area 115 of the substrate 110, and a signal sensing section 132 located in the sensing area 116 of the substrate 110. The material of the surface of the counter electrode 130 includes silver and silver halide, preferably silver chloride or silver iodine. Because the electrode material of the counter electrode 130 of the present invention includes silver and silver halide (Ag/AgX), the counter electrode 130 of the present invention includes functions of the counter electrode and the reference electrode of the common knowledge in the art. Specifically, the counter electrode 130 of the present invention can (1) form an electronic circuit with the working electrode 120 to cause the current between the counter electrode 130 and the working electrode 120 to be conducted to ensure that the electrochemical reaction occurs on the working electrode 120; and (2) provide a stable relative potential as a reference potential. Therefore, the working electrode 120 and the counter electrode 130 of the present invention form a 2-electrode system. In order to further reduce the cost and improve the biocompatibility of the biosensor of the present invention, the Ag/AgX can be used with carbon, for example, the Ag/AgX is mixed into carbon paste, and the content of the silver halide can be an amount that allows the counter electrode 130 to stably perform the measurement step. The surface of the counter electrode 130 can be partially covered by a conductive material to prevent silver halide from the dissolution and to protect the counter electrode 130, wherein the conductive material is selected from the material that does not affect the measuring result of the working electrode. For example, the conductive material is carbon.

In another embodiment, the biosensor is not limited to a wire-type or stacked-type electrode structure.

According to another embodiment of the present disclosure, the initial amount of the silver halide can be zero before the biosensor is ready for shipping out of the plant for sale. In this case the counter electrode 130 of the biosensor has no silver halide. After the biosensor is subcutaneously implanted in the patient and during the first replenishment period before the first measurement, the initial amount of the silver halide can be replenished by oxidizing the silver coated on the electrodes 130.

The chemical reagent 140 at least covers on the surface of the signal sensing section 122 of the working electrode 120. In other embodiment, the chemical reagent 140 further covers on the signal sensing section 132 of the counter electrode 130. That is to say, the counter electrode 130 is not covered by the chemical reagent 140. The sensing area 116 of the micro biosensor 100 can be implanted subcutaneously to cause the signal sensing section 122 of the working electrode 120 to measure the physiological signal of the analyte in the biofluid. The physiological signal is transmitted to the processor 210 through the signal output section 121 of the working electrode 120 to obtain the physiological parameter. In addition, apart from the transmitter 200, the physiological parameter can also be obtained from the user device 20 through the wire/wireless communication. The common user device 20 can be a smartphone, a physiological signal receiver or a blood glucose meter.

Figure 9:
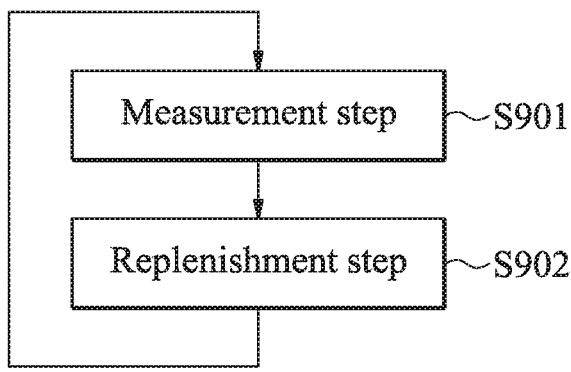
FIG. 9 shows a method of measuring an analyte according to an embodiment in the present invention.

Please refer to FIG. 2C, which is a sectional schematic diagram of a cut view of the micro biosensor along the section line A-A' in FIG. 2A, wherein the line A-A' is a section line of the sensing area 116 of the micro biosensor 100. In FIG. 2C, the working electrode 120 is disposed on the surface 111 of the substrate 110, the counter electrode 130 is disposed on the opposite surface 112 of the substrate 110, and the surfaces of the working electrode 120 and the counter electrode 130 are covered by the chemical reagent 140. Basically, the chemical reagent 140 covers at least part of the surface of the working electrode 120. The micro biosensor 100 of the present invention performs a measurement step during a measurement period, and performs a replenishment (regeneration) step during a replenishment period. When the measurement step is performed, a voltage level of the working electrode 120 is higher than that of the counter electrode 130, causing a current to flow from the working electrode 120 to the counter electrode 130, so that an oxidation reaction occurs on the working electrode 120 having an electrochemical reaction with the chemical reagent 140 and the analyte and the physiological signal is measured, and a reduction reaction occurs on the counter electrode 130, so that silver halide (AgX) in the counter electrode 130 is consumed and dissociated into silver (Ag) and halide ion ($X^-$). Because the silver halide in the counter electrode 130 is consumed, the silver halide needs to be replenished in the counter electrode 130 to perform the next measurement step. When the replenishment step is performed, the voltage level of the counter electrode 130 is higher than that of the working electrode 120, causing a current to flow from the counter electrode 130 to the working electrode 120, so that an oxidation reaction occurs on the counter electrode 130 to cause silver to combine with halide ion in the living body or $Cl^-$ oxided (or dissociated) from AgCl to replenish silver halide. The detailed measurement step and the detailed replenishment step are illustrated in FIG. 9.

Figure 3:
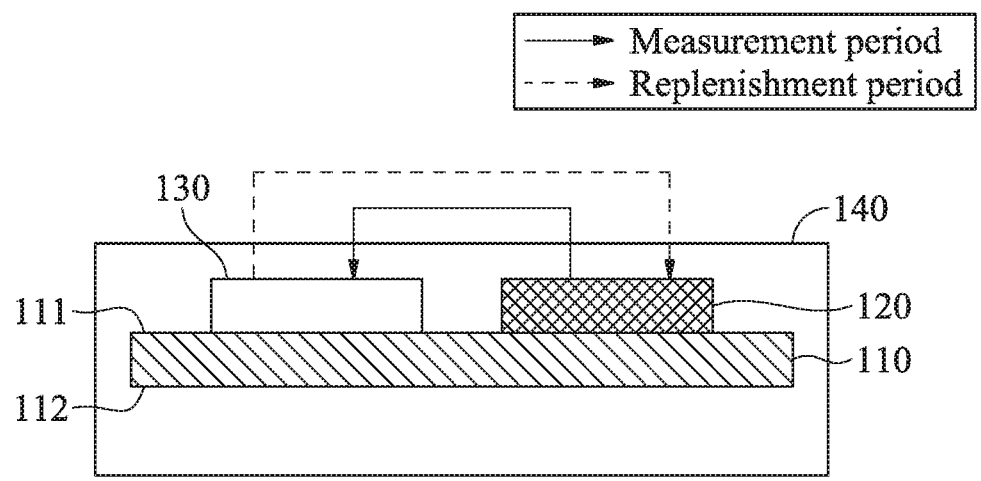
FIG. 3 shows a sectional schematic diagram of a second embodiment of the micro biosensor of the present invention.

In another embodiment, the working electrode 120 and the counter electrode 130 can be disposed on the same surface of the substrate 110. Specifically, both the working electrode 120 and the counter electrode 130 can be disposed on the surface 111 or the opposite surface 112 of the substrate 110, as shown in FIG. 3. Similarly, when the measurement step is performed, a current flows from the working electrode 120 to the counter electrode 130, so that an oxidation reaction occurs on the working electrode 120 and the physiological signal is measured, and silver halide (AgX) in the counter electrode 130 is consumed and dissociated into silver (Ag) and halide ion ($X^-$). When the replenishment step is performed, a current flows from the counter electrode 130 to the working electrode 120, so that an oxidation reaction occurs on the counter electrode 130 to cause the combination of silver and halide ion to replenish silver halide.

The detailed electrode stacks in FIGS. 2C and 3 are omitted, and only the electrode positions are shown.

In any embodiment above, to prevent the silver electrode material from breakage due to over chlorination, a layer of conductive material, such as carbon, can be further disposed between the opposite surface 112 of the substrate 110 and the silver of the counter electrode 130. However, if the bottom layer of the counter electrode 130 is carbon, the resistance at a switch position will be too high. A conductive layer, such as silver, can be further disposed between the carbon conductive material and the opposite surface 112 of the substrate 110. Therefore, the material of the counter electrode 130 of the present invention sequentially is the conductive layer, the carbon layer and the silver/silver halide layer from the opposite surface 112 of the substrate 110.

Switching Applications of a Constant Voltage Circuit

Figure 4A:
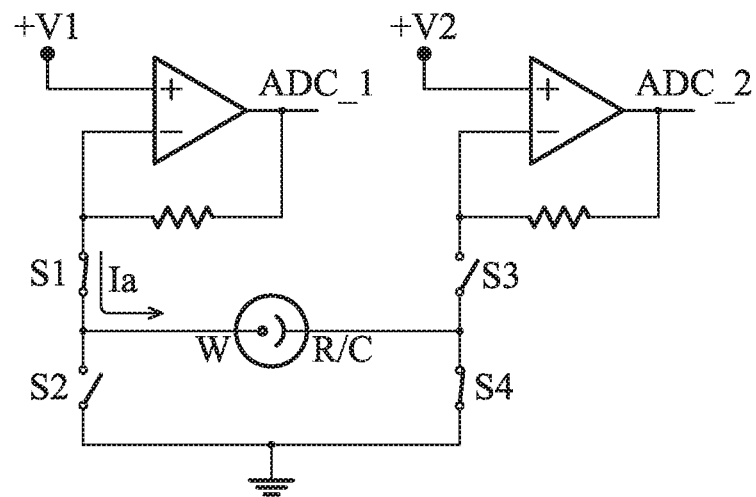
FIG. 4A shows a constant voltage circuit in a measurement mode in the present invention.
Figure 4B:
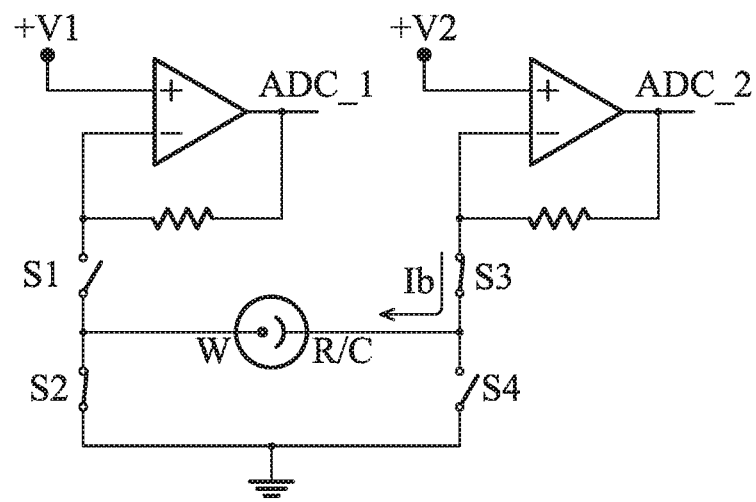
FIG. 4B shows a constant voltage circuit in a replenishment mode in the present invention.

Please refer to FIGS. 4A-B and FIGS. 5A-D, wherein FIGS. 4A and 4B show a constant voltage circuit in a measurement mode and a replenishment mode, respectively, in the present invention, and FIGS. 5A-D respectively show the current schematic diagrams of the constant voltage circuit running in the measurement mode and the replenishment mode by turns in different ways. The measurement mode can be started and stopped by applying a measurement potential difference V1 and removing the measurement potential difference V1, respectively, and the corresponding current is represented by Ia. In the measurement mode, the measurement potential difference V1 is applied across the working electrode W and the counter electrode R/C during the measurement period T1, so that the voltage of the working electrode W is higher than that of the counter electrode R/C. During the measurement mode, as shown in FIG. 4A, the switches S1 and S4 are in the close circuit state, the switches S2 and S3 are in the open circuit state, the working electrode W is +V1, and the counter electrode R/C is grounded, so that at the working electrode W, an oxidation reaction occurs, and the working electrode W electrochemically reacts with chemical reagents and an analyte to output a physiological signal Ia. The AgCl in the counter electrode R/C has a consumption amount corresponding to the physiological signal Ia. As shown in FIGS. 5A-5D, between any two of a plurality of measurement periods T1 is a period T2 during which no measurement is performed. In some preferred embodiments, T2 is a constant value.

The replenishment mode can be started and stopped by applying a replenishment potential difference V2 and removing the replenishment potential difference V2, respectively, and the corresponding current is represented by Ib. V2 is a constant value in a range of 0.1V to 0.8V, preferably range of 0.2V to 0.5V. In the replenishment mode, the replenishment potential difference V2 is applied across the working electrode W and the counter electrode R/C during the replenishment period t2 (t2 is in a range of 0 to T2), so that the voltage of the counter electrode R/C is higher than that of the working electrode W. During the replenishment mode, as shown in FIG. 4B, the switches S1 and S4 are in the open circuit state, the switches S2 and S3 are in the close circuit state, the working electrode W is grounded, and the counter electrode R/C is +V2, so that on the counter electrode R/C, an oxidation reaction of Ag occurs to replenish the counter electrode R/C with AgCl by a replenishment amount. In the constant voltage circuit, the replenishment potential difference V2 is a constant voltage, and the measured output current is Ib. In the present invention, the amount or value of capacity (with the unit "coulomb" and represented by the symbol "C") of AgCl is defined by calculating the area under the current curve, so the consumption amount of AgCl in the measurement mode is Ia*T1, and the replenishment amount of AgCl in the replenishment mode is Ib*t2. In such case, the replenishment amount of AgCl can be controlled by adjusting the period t2 during which the potential difference V2 is applied. In other words, on the premise that the AgCl on the counter electrode R/C is kept within the safe storage range, the replenishment amount can be equal to or not equal to (including approximately similar, greater than or less than) consumption amount.

Figure 5A:
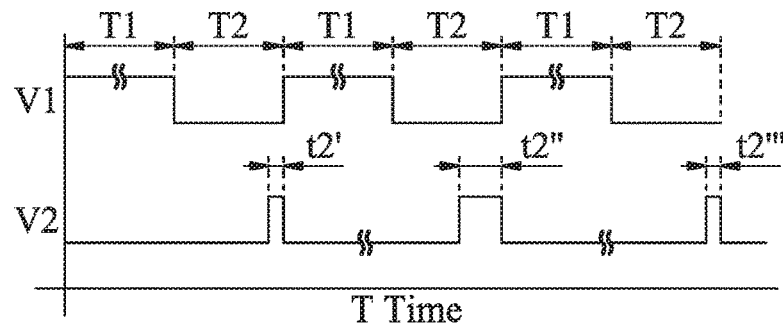
FIG. 5A shows a current schematic diagram of the constant voltage circuit running in the measurement mode and the replenishment mode by turns in a first way.

In FIGS. 5A-5D, the horizontal axis represents time, the curve for V1 represents the application and removal of the measurement potential difference V1, and the curve for V2 represents the application and removal of the replenishment potential difference V2. Please refer to FIG. 5A. In a preferred embodiment, both V2 and T2 are constant values, and the period t2 (i.e., the replenishment period) during which V2 is applied is a variable value. The replenishment period t2 is dynamically adjusted in a range of 0 to T2 according to the physiological signal Ia measured in the measurement mode and during the measurement period T1. As shown in FIG. 5A, t2 can be t2', t2" or t2'''.... In other words, the replenishment period t2 can be changed according to the consumption amount of AgCl. In the condition of a high consumption amount of AgCl, the counter electrode R/C can be replenished for a longer time to keep the AgCl on the counter electrode R/C within the safe storage range. For example, the amount of AgCl replenished during t2" will be greater than the amount of AgCl replenished during t2'.

Figure 5B:
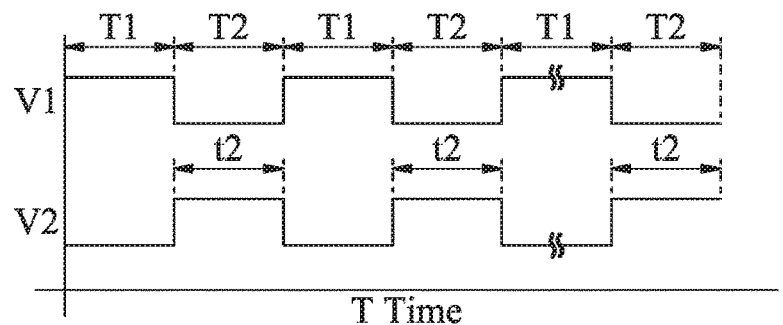
FIG. 5B shows a current schematic diagram of the constant voltage circuit running in the measurement mode and the replenishment mode by turns in a second way.
Figure 5C:
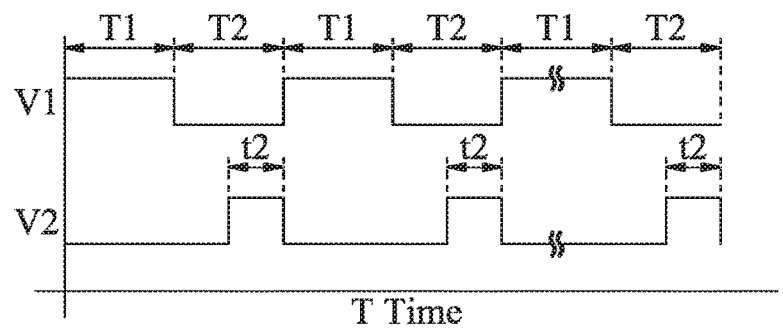
FIG. 5C shows a current schematic diagram of the constant voltage circuit running in the measurement mode and the replenishment mode by turns in a third way.
Figure 5D:
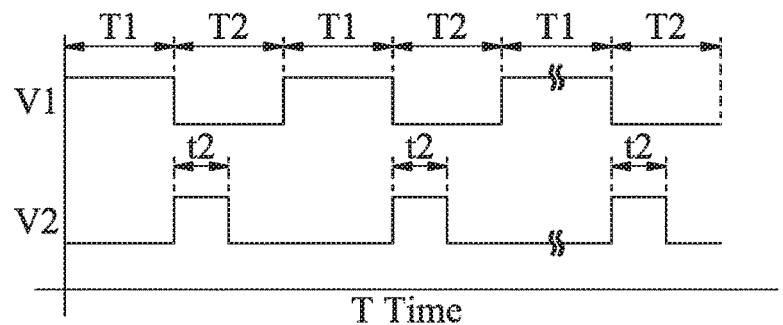
FIG. 5D shows a current schematic diagram of the constant voltage circuit running in the measurement mode and the replenishment mode by turns in a fourth way.

Please refer to FIG. 5B, in another preferred embodiment, V2, T2 and t2 are all constant values, wherein t2=T2. That is, the measurement mode and replenishment mode alternate seamlessly, and the period during which no measurement is performed is the replenishment period. Please refer to FIGS. 5C and 5D, in some preferred embodiments, V2, T2, and t2 are constant values, wherein t2 is a constant value greater than 0 and less than T2. For example, t2=½ T2, ⅖ T2, ⅗ T2, etc. The difference between FIG. 5C and FIG. 5D is that in FIG. 5C, after each measurement mode, a buffer time (buffer time=T2−t2) is passed before the replenishment mode starts; and in FIG. 5D, after each measurement mode, the replenishment mode starts immediately without any buffer time, and there is a period of time between the end of each replenishment mode and the start of the next measurement mode. In some preferred embodiments, t2 is less than T2, and t2 can be any time period during T2.

Figure 5E:
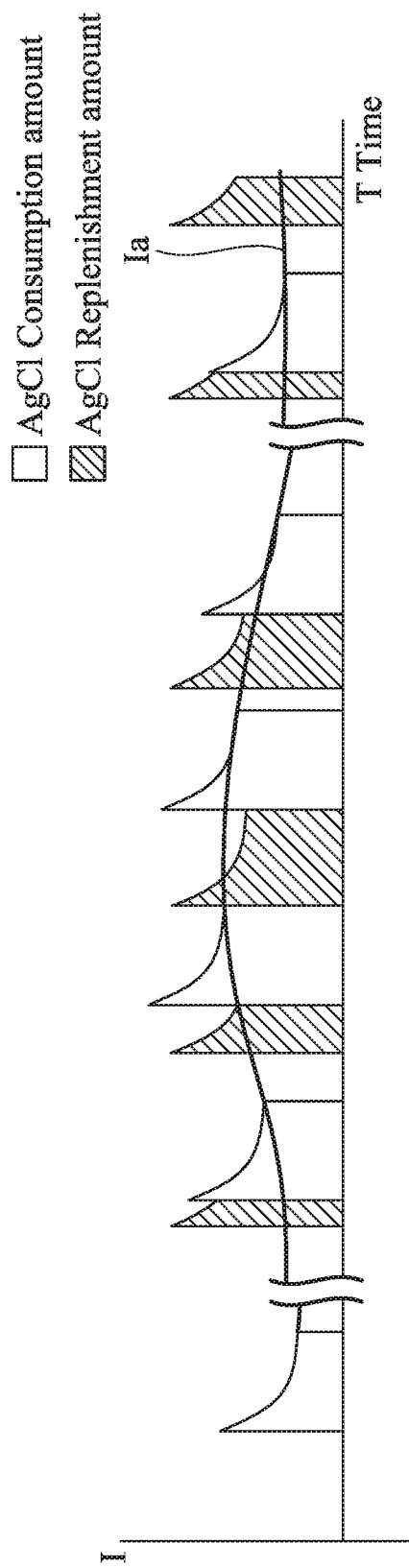
FIG. 5E shows a current schematic diagram of the constant voltage circuit running in the measurement mode and the replenishment mode by turns in a fifth way.
Figure 5F:
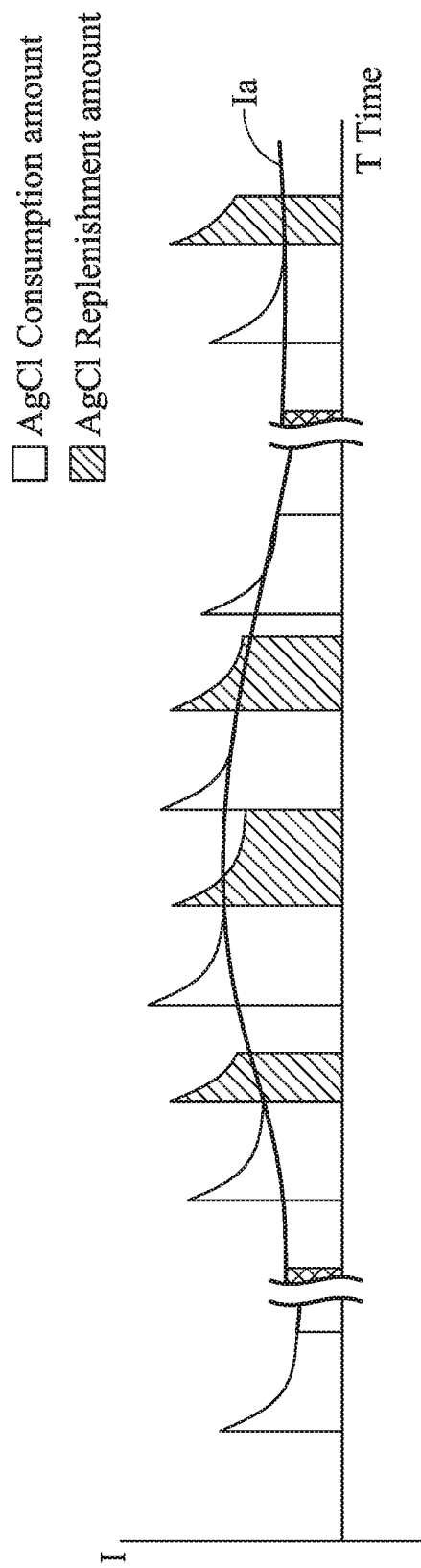
FIG. 5F shows a current schematic diagram of the constant voltage circuit running in the measurement mode and the replenishment mode by turns in a sixth way.

Please refer to FIGS. 5E and 5F, which show current-time schematic diagrams of the constant voltage circuit running in the measurement mode and the replenishment mode by turns in different ways. In FIGS. 5E and 5F, the horizontal axis represents time, the vertical axis represents current, and the curve represents the physiological parameter curve calculated from the measured physiological signal Ia. In the two embodiments, similar to that in FIG. 5A, V2 and T2 are constant values and the replenishment period t2 is a variable value. In FIGS. 5E and 5F, the white area under the curve represents the AgCl consumption amount in the measurement mode (Ia*T1), and the oblique area represents the replenishment amount of AgCl in the replenishment mode (Ib*t2). It can be seen from the figures that in order to make Ib*t2 close to Ia*T1 or within a certain range of Ia*T1, the replenishment period t2 is dynamically adjusted in a range of 0 to T2 according to the measured physiological signal Ia and the measurement period T1. According to requirements, the front part (as shown in FIG. 5E) or the back part (as shown in FIG. 5F) of the period (T2) where the measurement mode is not executed can be selected to perform the replenishment mode.

Switching Applications of a Segmental Constant Current Circuit

Figure 6A:
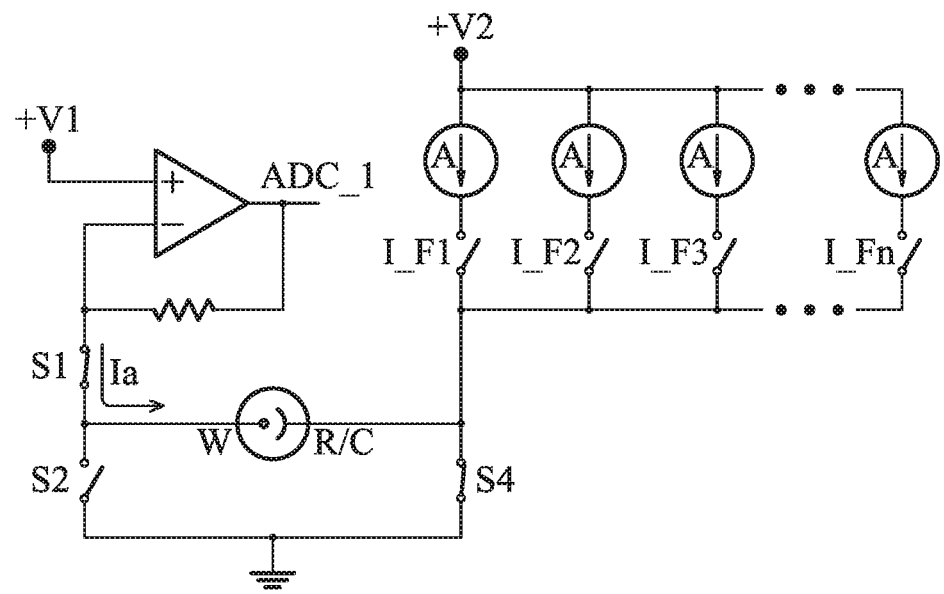
FIG. 6A shows a segmental constant current circuit in a measurement mode in the present invention.
Figure 6B:
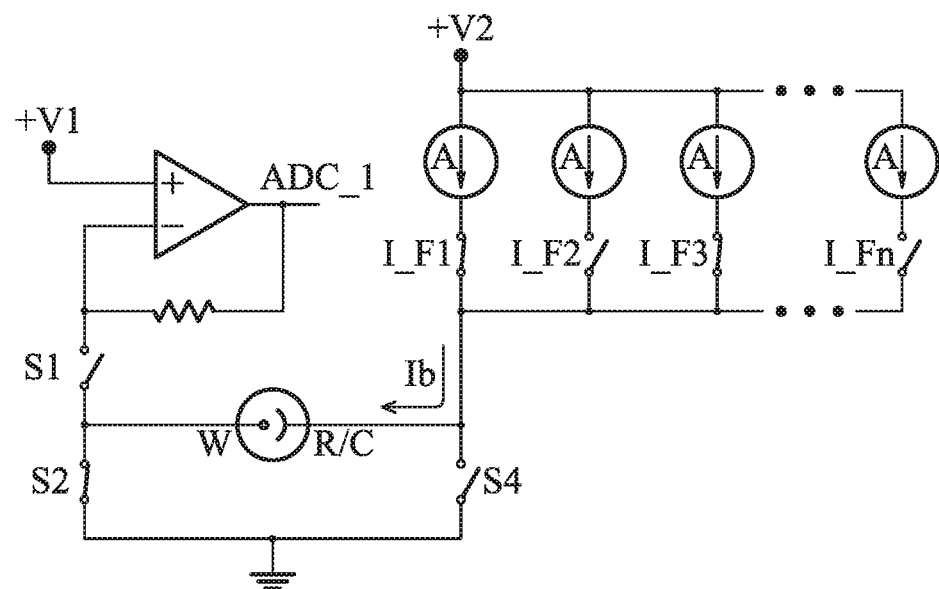
FIG. 6B shows a segmental constant current circuit in a replenishment mode in the present invention.
Figure 8A:
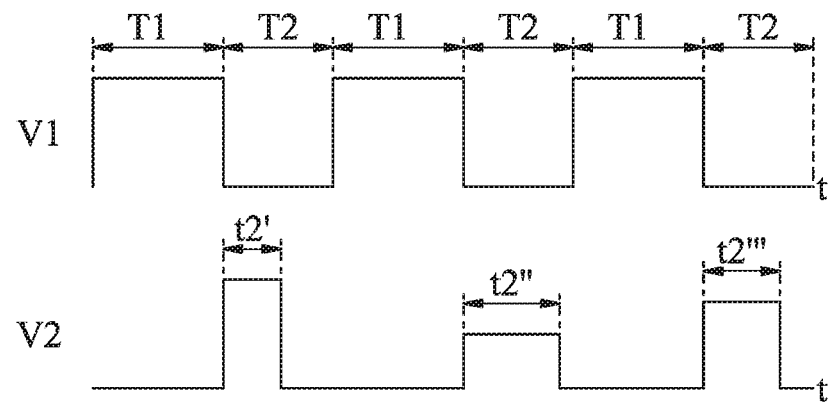
FIG. 8A shows a voltage schematic diagram of the constant current circuit running in the measurement mode and the replenishment mode by turns in a first way.
Figure 8B:
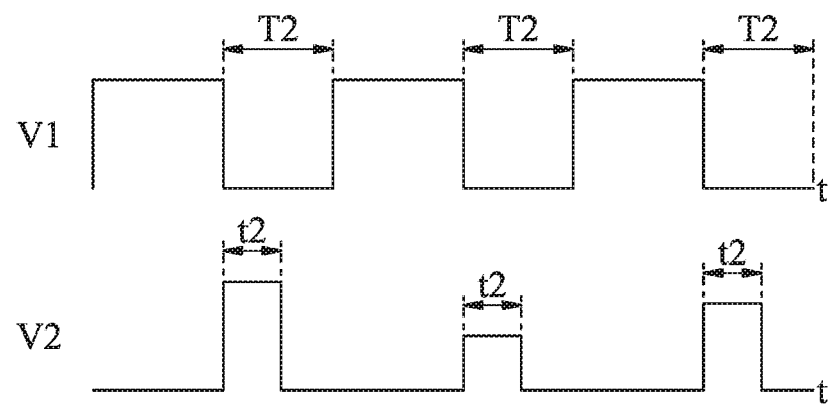
FIG. 8B shows a voltage schematic diagram of the constant current circuit running in the measurement mode and the replenishment mode by turns in a second way.
Figure 8C:
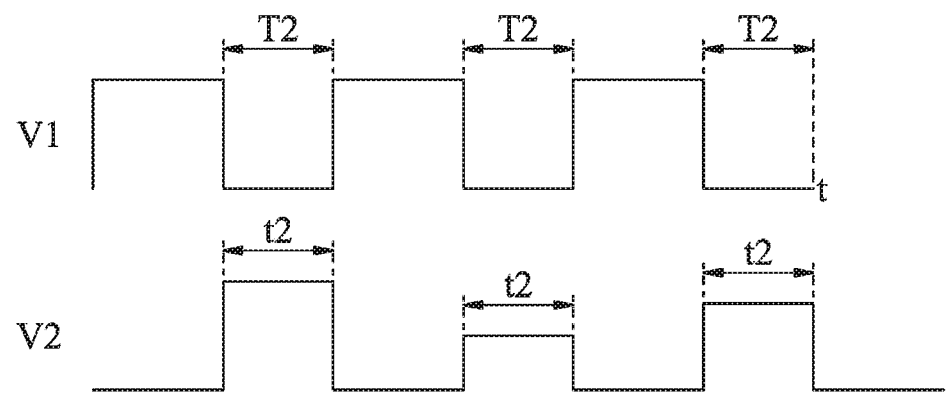
FIG. 8C shows a voltage schematic diagram of the constant current circuit running in the measurement mode and the replenishment mode by turns in a third way.

Please refer to FIGS. 6A-6B and FIGS. 8A-C, wherein FIGS. 6A and 6B show a segmental constant current circuit in a measurement mode and a replenishment mode, respectively, according to the present invention, and FIGS. 8A-C respectively show the voltage schematic diagrams of the constant current circuit running in the measurement mode and the replenishment mode by turns in different ways. The measurement mode can be started and stopped by applying a measurement potential difference V1 and removing the measurement potential difference V1, respectively, and the corresponding current is represented by Ia. In the measurement mode, the measurement potential difference V1 is applied across the working electrode W and the counter electrode R/C during the measurement period T1. During the measurement mode, as shown in FIG. 6A, the switches S1 and S4 are in the close circuit state, the remaining switches are in the open circuit state, the working electrode W is +V1, and the counter electrode R/C is grounded, so that at the working electrode W, an oxidation reaction occurs, and the working electrode W electrochemically reacts with chemical reagents and an analyte to output a physiological signal Ia. The AgCl in the counter electrode R/C has a consumption amount corresponding to the physiological signal Ia. As shown in FIGS. 8A-C, between any two of a plurality of measurement periods T1 is a period T2 during which no measurement is performed. In some preferred embodiments, T2 is a constant value.

The replenishment mode can be started and stopped by applying a replenishment potential difference V2, which is a variable value, and removing the replenishment potential difference V2, respectively, and the corresponding current is represented by Ib. In the replenishment mode, the replenishment potential difference V2 is applied across the working electrode W and the counter electrode R/C during the replenishment period t2 (wherein t2 is in a range of 0 to T2). During the replenishment mode, as shown in FIG. 6B, the switches S1 and S4 are in the open circuit state, the switch S2 and at least one of switches corresponding to I_F1 to I_Fn are in the close circuit state (wherein FIG. 6B exemplarily shows that the switches corresponding to I_F1 and I_F3 are in the close circuit state), the working electrode W is grounded, and the counter electrode R/C is +V2, so that on the counter electrode R/C, an oxidation reaction of Ag occurs to replenish the counter electrode R/C with AgCl. In the replenishment mode, according to the magnitude of the physiological signal Ia and the measurement period T1, at least one of the switches corresponding to I_F1 to I_Fn can be selected to be turned on to output a constant current Ib, and the replenishment amount of AgCl can be controlled by adjusting the period t2 during which the potential difference V2 is applied. That is, on the premise that the AgCl on the counter electrode R/C is kept within the safe storage range, the replenishment amount can be equal to or not equal to (including approximately similar, greater than or less than) consumption amount.

Switching Applications of a Continuous Variable Constant Current Circuit

Figure 7A:
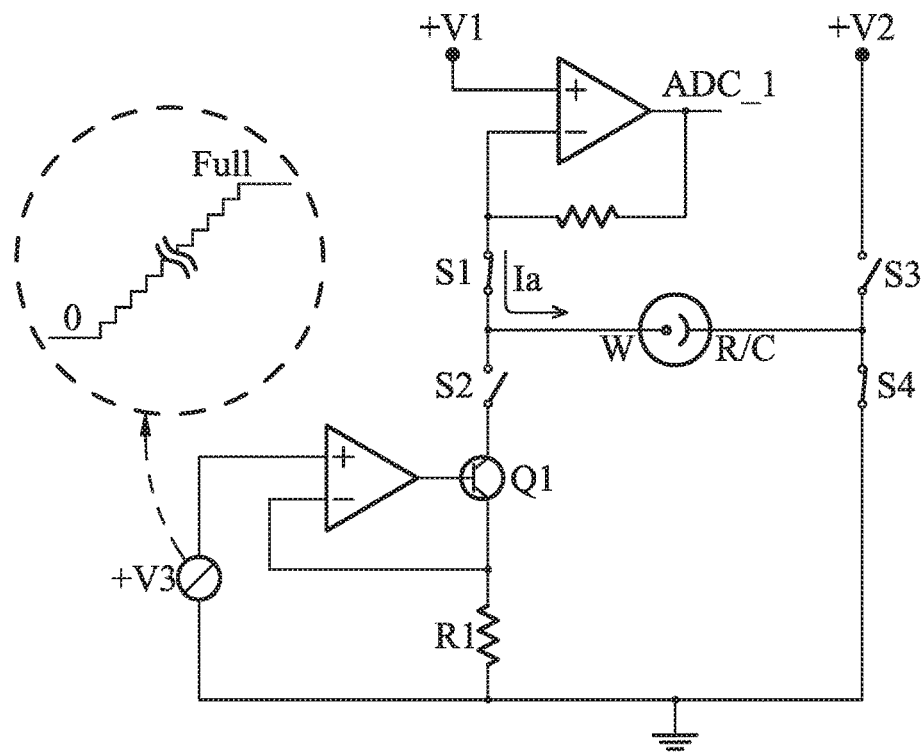
FIG. 7A shows a continuous variable constant current circuit in a measurement mode in the present invention.
Figure 7B:
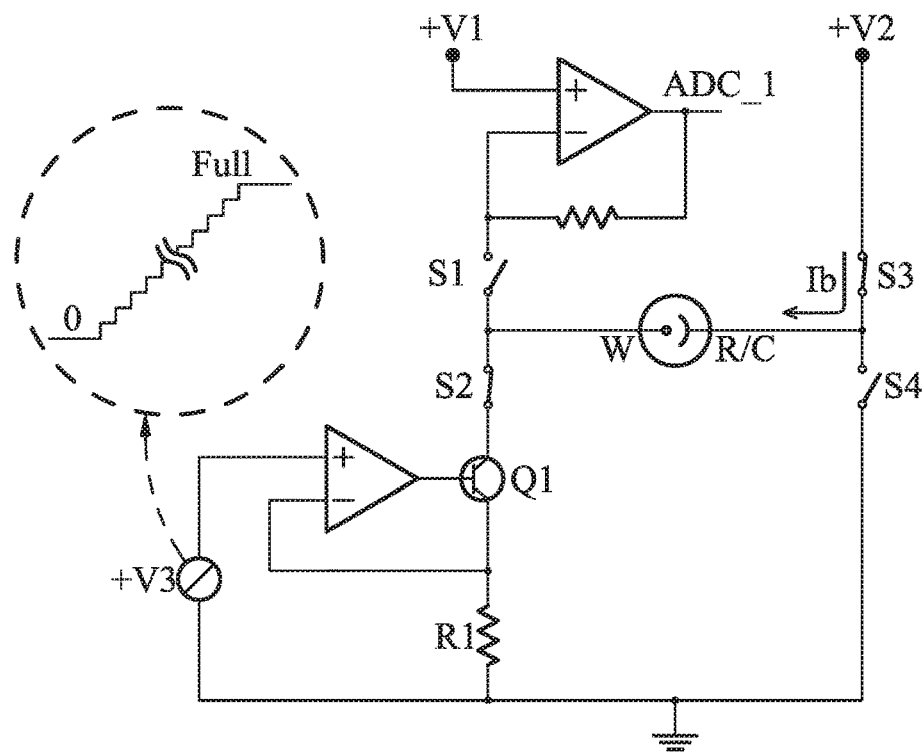
FIG. 7B shows a continuous variable constant current circuit in a replenishment mode in the present invention.

Please refer to FIGS. 7A-7B and FIGS. 8A-8C, wherein FIGS. 7A and 7B show a continuous variable constant current circuit in a measurement mode and a replenishment mode, respectively, according to the present invention. The measurement mode and the replenishment mode in this embodiment are similar to those in FIGS. 6A and 6B, so they will not be repeated here. This embodiment differs from that in FIGS. 6A and 6B only in that in the replenishment mode, according to the magnitude of the physiological signal Ia, a constant current Ib can be output by the control of the digital-to-analog converter (DAC), and the replenishment amount of AgCl can be controlled by adjusting the period t2 during which the potential difference V2 is applied. That is, on the premise that the AgCl on the counter electrode R/C is kept within the safe storage range, the replenishment amount can be equal to or not equal to (including approximately similar, greater than or less than) consumption amount.

In FIGS. 8A-C, the horizontal axis represents time, the vertical axis represents current, the curve for V1 represents the application and removal of the measurement potential difference V1, and the curve for V2 represents the application and removal of the replenishment potential difference V2. Please refer to FIG. 8A, in a preferred embodiment, T2 is a constant value, V2 and the period t2 (i.e., the replenishment period) during which V2 is applied are variable values. The replenishment period t2 is dynamically adjusted in a range of 0 to T2 according to the measurement period T1 and the physiological signal Ia measured in the measurement mode. As shown in FIG. 8A, t2 can be t2', t2" or t2'" . . . . In other words, the replenishment period t2 can be changed according to the consumption amount of AgCl. In the condition of a high consumption amount of AgCl, the counter electrode R/C can be replenished for a longer time to keep the AgCl on the counter electrode R/C within the safe storage range.

Please refer to FIG. 8B, in another preferred embodiment, V2 is a variable value, and T2 and t2 are constant values, wherein t2 is a constant value greater than 0 and less than T2. For example, t2 can be ½ T2, ⅖ T2, ⅗ T2, etc. In this embodiment, V2 is dynamically adjusted according to the consumption amount of AgCl in the step of measuring the physiological signal (i.e., in the measurement mode). One example of the dynamic adjustment method is as follows. For example, the segmental constant current circuit is used. The circuit includes n constant current supplies and n switches, and each constant current supply corresponds to a switch. In the replenishment mode, according to the consumption amount of AgCl, at least one of the n switches is selected to be turned on (i.e., in the close circuit state) to output a constant current value. When the replenishment period t2 is a constant value, the replenishment amount of AgCl can be controlled by selecting different constant current outputs.

Please refer to FIG. 8C, in another preferred embodiment, V2 is a variable value, T2 and t2 are constant values, wherein t2=T2. That is, the measurement mode and replenishment mode alternate seamlessly, and the period during which no measurement is performed is the replenishment period.

Compared with the continuous variable constant current circuit, in the segmental constant current circuit, multiple current paths can be controlled through multiple switches, and thus the replenishment can be performed by multi-segment constant current according to the amount of current required. The multi-segment constant current, in this way, saves electricity and can reduce costs. In addition, whether it is a constant voltage circuit or a constant current circuit, the potential difference can come from a DC power supply or an AC power supply, preferably from a DC power supply.

The embodiments of FIGS. 5A to 8C all involve the operation manner of alternately cycling measurement step and replenishment step, which means that there is an AgCl replenishment step between any two measurement steps. Such manner can better ensure that AgCl remains within the safe storage range. However, in some preferred embodiments, Y times of AgCl replenishment can be optionally performed during N measurements, where Y≤N, in such a way that the accumulated replenishment amount of AgCl can still be kept within the safe storage range. The measurement step and the replenishment step do not necessarily need to be performed in an alternate cycle. A replenishment step can also be performed after several measurement steps, or after a predetermined measurement time. For example, a replenishment step can be performed after 10 measurement steps, or after the accumulated measurement time reaches 1 hour.

Figure 8D:
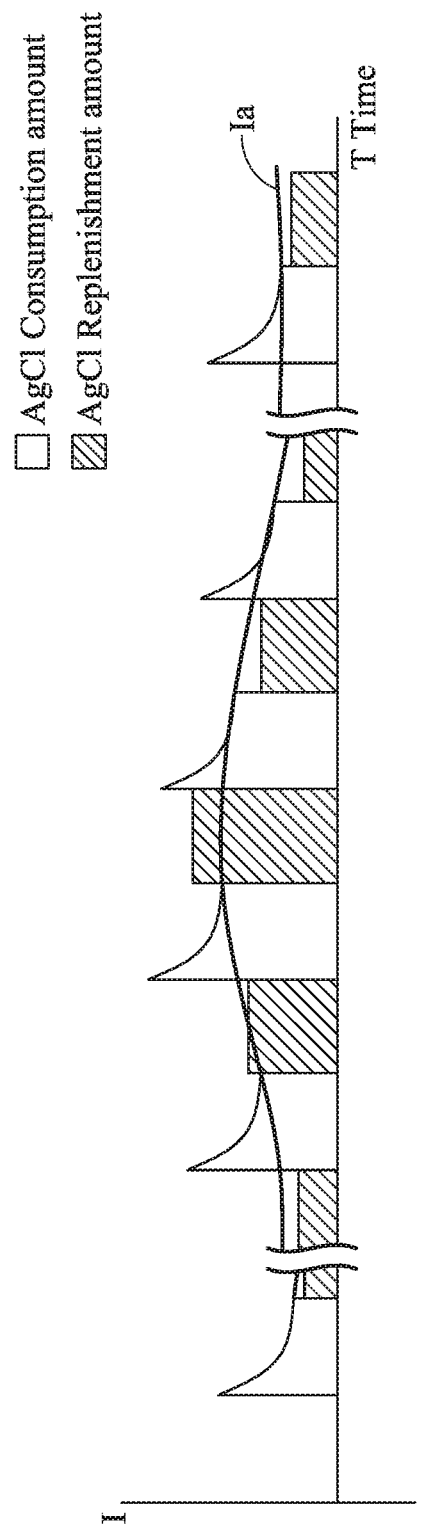
FIG. 8D shows a schematic diagram of the constant current circuit running in the measurement mode and the replenishment mode by turns in a third way.

Please refer to FIG. 8D, which shows a current-time schematic diagram of the constant current circuit running in the measurement mode and the replenishment mode by turns in a way similar to that of FIG. 8C. In FIG. 8D, the curve represents the physiological parameter curve calculated from the measured physiological signal Ia, the conditions of T2 and t2 being both constant values and V2 being a variable value are similar to those in FIG. 8C. In FIG. 8D, the white area under the curve represents the AgCl consumption amount in the measurement mode (Ia*T1), and the oblique area represents the replenishment amount of AgCl in the replenishment mode (Ib*t2). It can be seen from this figure that in order to make Ib*t2 close to Ia*T1 or within a certain range of Ia*T1, the replenishment potential difference V2 is dynamically adjusted according to the consumption amount of AgCl.

In addition, although FIGS. 5E, 5F, and 8D do not show the output timing of each physiological parameter value after each measurement step for measuring a physiological signal is performed, the physiological parameter value may be output, but is not limited to, when the measurement is completed or during the replenishment period and the AgCl replenishment step may be performed after every physiological parameter is output or after obtaining the physiological signal, but is not limited thereto.

Please refer to FIG. 9, which shows a method of measuring an analyte according to the present invention. A usage lifetime of a micro biosensor can be prolonged by the method. The micro biosensor, which may be, for example, the micro biosensor shown in FIG. 2A to FIG. 3, is used to be implanted subcutaneously to measure a physiological signal representative of a physiological parameter associated with the analyte in a biofluid (such as tissue fluid). In the embodiment of FIG. 9, the analyte can be glucose in the tissue fluid, the physiological parameter is the glucose level in the human body, and the physiological signal is a current value measured by the micro-biological sensor. In this embodiment, the method for measuring the analyte includes repeatedly performing the measurement step (S901) and the replenishment step (S902). The measurement step (S901) includes using the aforementioned constant voltage circuit or the constant current circuit to perform the aforementioned measurement mode during the measurement period T1 to output a physiological signal (i.e., a current value), and at the same time, the AgCl on the counter electrode has a consumption amount corresponding to the current value. The measurement step (S901) also includes stopping the measurement step by stopping the measurement mode, and the current value is calculated to output a physiological parameter (i.e., glucose level).

In the measurement step (S901), the chemical equations are as follows.
The following oxidation reactions occur at the working electrode 120.
Glucose+Glucose oxidase (Gox, which is an flavin adenine dinucleotide (FAD) enzyme)$\leftrightarrows$Gluconolactone+$FADH_2$
$FADH_2+O_2 \leftrightarrows FAD+H_2O_2$
$H_2O_2 \leftrightarrows 2H^+ + O_2 + 2e^-$ The following reduction reactions occur at the counter electrode 130.
$2AgCl+2e^- \leftrightarrows 2Ag+2Cl^-$ The replenishment step (S902) includes using the aforementioned constant voltage circuit or constant current circuit to perform the aforementioned replenishment mode during the replenishment period, such that the AgCl on the counter electrode has a replenishment amount corresponding to consumption amount, and thus the AgCl on the counter electrode has an amount controlled within a safe storage range. As a result, the potential difference between the working electrode and the counter electrode can be kept stable, so that the obtained current value can still maintain a stable correlation with the glucose value (if the detected substance is other analytes, the correlation may be proportional or inverse correlation). In other words, it is possible to keep a stable correlation between a next current value obtained in a next measurement step and a next glucose value. The replenishment step (S902) also includes a step of stopping the replenishment step by stopping the aforementioned replenishment mode. After the replenishment step (S902) is finished, the method returns to the measurement step (S901) until N measurement steps (S901) and N replenishment steps (S902) are executed.

In the replenishment step (S902), the chemical equations are as follows. The following reduction reactions occur at the working electrode 120.
Glucose+Glucose oxidase (Gox, which is an flavin adenine dinucleotide (FAD) enzyme)$\leftrightarrows$Gluconolactone+$FADH_2$
$FADH_2+O_2 \leftrightarrows FAD+H_2O_2$
$H_2O_2+2H^++2e^- \leftrightarrows H_2O$
$O_2+4H^++4e^- \leftrightarrows 2H_2O$ The positive potential on the counter electrode 130 causes the following oxidation reactions occurring at the counter electrode 130.
$2Ag \leftrightarrows 2Ag^+ + 2Cl^- \leftrightarrows 2AgCl+2e^-$ The Ag on the counter electrode is oxidized to $Ag^+$ and combined with $Cl^-$ from the body or from oxidation (or dissociation) of AgCl to form AgCl, such that part or all of the AgCl consumed during the measurement period T1 is replenished onto the counter electrode.

Human can intake chloride ions and iodide ions through iodine-doped salts. The available halide ions include at least chloride ions and iodide ions for replenishing the counter electrode with silver halide.

The following embodiments are directed to cycles of N measurement steps (S901) and N replenishment steps (S902). The physiological parameter mentioned is preferably a glucose value, and the physiological signal mentioned is preferably a current value. According to some preferred embodiments, each measurement potential difference V1 is applied during the measurement period T1, each replenishment potential difference V2 is applied during the replenishment period t2, and the measurement period T1 is a constant value, which can be a value within 3 seconds, 5 seconds, 10 seconds, 15 seconds, 30 seconds, 1 minute, 2.5 minutes, 5 minutes, or 10 minutes. According to some preferred embodiments, the constant value may be a value within 30 seconds. The measurement period T1 is a constant value, and can be 2.5 seconds, 5 seconds, 15 seconds, 30 seconds, 1 minute, 2.5 minutes, 5 minutes, 10 minutes, or 30 minutes, preferably 30 seconds. According to some preferred embodiments, each measurement period T1 plus each replenishment period t2 is a constant value. According to some preferred embodiments, each replenishment potential difference V2 has a constant voltage value, and each replenishment period t2 is dynamically adjusted according to each consumption amount of AgCl (as shown in FIG. 5A). According to some preferred embodiments, each output physiological parameter is obtained through calculation of the physiological signals at a single measurement time point in each measurement period T1. According to some preferred embodiments, each output physiological parameter is obtained through a mathematical operation value of a plurality of physiological signals at a plurality of measurement time points in each measurement period T1. The aforementioned mathematical operation value is, for example, a accumulated value, an average value, a median value, an average value of median, and so on. According to some preferred embodiments, the replenishment amount of AgCl on the counter electrode is controlled within a safe storage range by controlling each replenishment amount to be equal to or not equal to (including approximately similar, greater than or less than) each consumption amount. As a result, a next physiological signal obtained during a next measurement step maintains a stable proportional correlation with a next physiological parameter. According to some preferred embodiments, the step of removing each measurement potential difference V1 is to disconnect the circuit that connects the working electrode and the counter electrode, or set each measurement potential difference V1 to zero. In other words, the power can be turned off to make the measurement circuit have an open circuit state; or, a 0 volt voltage can be applied across the working electrode and the counter electrode, wherein the operation time of either of the two operations is 0.01~0.5 seconds. The step of removing the measurement potential difference V1 can avoid the generation of Λ-shaped physiological signals. According to some preferred embodiments, the step of removing each replenishment potential difference V2 is to disconnect the circuit configured to connect the working electrode and the counter electrode, or set each replenishment potential difference V2 to zero.

According to some preferred embodiments, after the biosensor is implanted in the human body, a warm-up time is required for the biosensor to be in the condition of equilibrium and stability in the body in order to stably present a physiological signal that is positively correlated with an analyte concentration. Therefore, in the measurement step (S901), the measurement voltage is continuously applied until the end of the measurement period T1, and the measurement period T1 is controlled such that the physiological signal and the physiological parameter of the analyte have a stable proportional correlation. To this end, the measurement period T1 can be a variable value or a combination of a variable value and a constant value (for example, a variable value plus a constant value, in which the variable value may be 1 hour, 2 hours, 3 hours, 6 hours, 12 hours or 24 hours, and the constant value may be, for example, 30 seconds).

Please refer to FIGS. 5A-F, 8A-D and 9. The present invention uses a voltage applied to the counter electrode R/C during a period to measure a resultant current of the counter electrode, and the initial capacity of AgCl is obtained by mathematical calculation of the resultant current during the period. For example, the initial capacity of AgCl is defined by calculating area under a curve of the resultant current. The initial capacity of AgCl is also referred to as the initial amount or initial coulomb amount ($C_{initial}$), the following are all described by amount. The counter electrode R/C contains Ag and AgCl. When the amount of AgCl (X % AgCl) is known, the amount of Ag can be calculated (Y % Ag=100%−X % AgCl). In each measurement step (S901), the consumption amount of AgCl (denoted by $C_{consume}$) is defined by calculating the area under the current curve of the working electrode W. The AgCl of the counter electrode R/C has a consumption amount $C_{consume}$ corresponding to the physiological signal Ia, i.e., $C_{consume}$=Ia*T1. In each replenishment step (S902), each replenishment amount (denoted by $C_{replenish}$) of AgCl is defined by calculating the area under the current curve of the counter electrode R/C, i.e., $C_{replenish}$=Ib*t2, where t2 is a value in a range of 0~T2.

The calculation method of AgCl safe storage amount is described below. In some preferred embodiments, the safe storage range is represented by the ratio of Ag to AgCl. The present invention uses the coulomb amount (C) measured at the counter electrode to reflect the ratio of Ag to AgCl. In some preferred embodiments, the ratio of Ag to AgCl is 99.9%:0.1%, 99%:1%, 95%:5%, 90%:10%, 70%:30%, 50%:50%, 40%:60% or 30:70%, which assure of a certain amount of the AgCl on the counter electrode without being exhausted, and thus each measurement step for measuring the physiological signal can be performed stably. The remaining amount of AgCl is the sum of the replenishment amount and the initial amount minus the consumption amount. In some preferred embodiments, the remaining amount of AgCl varies within a range, that is, the remaining amount of AgCl is controlled within a range of the initial amount plus or minus a specific value (X value). Namely, ($C_{replenish}$+$C_{initial}$)−$C_{consume}$=$C_{initial}$±X, where 0<X<100% $C_{initial}$, 10% $C_{initial}$<X≤90% $C_{initial}$, or 0.5% $C_{initial}$<X≤50% $C_{initial}$. In some preferred embodiments, the remaining amount of AgCl may, within a range, gradually decrease, gradually increase, change steadily, or change arbitrarily but still within the range.

Figure 10:
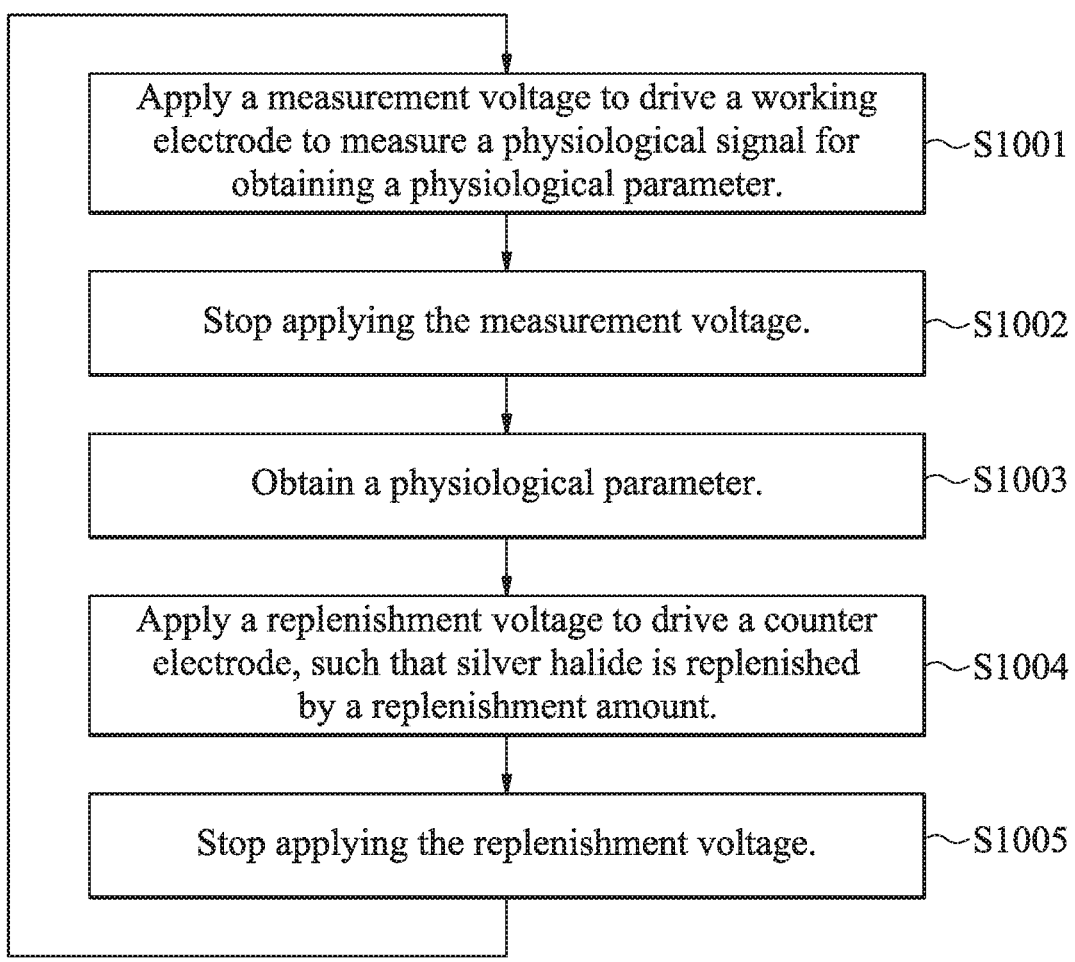
FIG. 10 shows a method of measuring an analyte according to another embodiment in the present invention.

Please refer to FIG. 10, which shows a method for measuring an analyte according to another embodiment of the present invention. Through this method, the usage lifetime of the micro biosensor can be prolonged and the amount of silver and silver halide materials of the counter electrode can be reduced. The micro biosensor, which may be, for example, the micro biosensor shown in FIG. 2A-FIG. 3, is used to be implanted subcutaneously to measure a physiological signal representative of a physiological parameter associated with the analyte in a biofluid (such as tissue fluid). The electrode material of the counter electrode of the micro biosensor includes silver and silver halide. In the embodiment of FIG. 10, the analyte can be glucose in tissue fluid, the physiological parameter is the glucose value in the human body, and the physiological signal is a current value measured by the micro biosensor. Only one cycle of this embodiment is described below. The method of this embodiment starts with the step of applying a measurement voltage to drive a working electrode to measure a physiological signal for obtaining a physiological parameter, wherein a specific amount of silver halide is consumed (hereinafter referred to as "consumption amount") (S1001).

Then the step of applying the measurement voltage is stopped (S1002), and the obtained physiological signal is used to obtain a physiological parameter (S1003). After the physiological parameter is obtained, a replenishment voltage is applied across a counter electrode and a working electrode to drive a counter electrode, such that silver halide is replenished by a replenishment amount (S1004), wherein a value (i.e., the aforementioned "remaining amount") of a sum of the replenishment amount and an initial amount minus the consumption amount is controlled within a range of the initial amount plus or minus a specific value. The above control step is achieved by controlling the replenishment amount to be equal to or not equal to (including approximately similar, greater than or less than) the consumption amount so as to maintain the amount of silver halide within a safe storage range. According to the chemical equations, the increase or decrease of the mole number of silver halide corresponds to the increase or decrease of the mole number of silver. Therefore, for the ease of descriptions, the consumption amount of silver halide corresponds to a simulated increased amount of silver. In some preferred embodiments, a value of the remaining amount is controlled such that the ratio of the amount of silver halide to the sum of the amount of silver halide plus the amount of silver (AgCl/Ag+AgCl) is greater than 0 and less than 1 (which means that there should be a certain amount of silver halide in the counter electrode), preferably between 0.01-0.99, between 0.1-0.9, between 0.2-0.8, between 0.3-0.7, or between 0.4-0.6. When the replenishment amount is reached, the step of applying the replenishment voltage is stopped (S1005). Then the method returns to step S1001 to execute the next loop.

A specific embodiment of the present invention will be described below. Taking a usage lifetime of a biosensor must reach 16 days as an example. To this end, the method to calculate the required size of Ag/AgCl material on a signal sensing section of a electrode is described below. For example, the average of the measured current of the analyte for each measurement is 30 nA, the measurement period (T1) is 30 seconds, and the replenishment period (t2) is 30 seconds. The daily consumption amount of AgCl ($C_{consume/day}$)=1.3 mC/day. Assuming that the requirement of a usage lifetime of a biosensor is 16 days, the consumption amount of AgCl required for using 16 days is 1.3× 16=20.8 mC.

For example, the length of the counter electrode is 2.5 mm, which corresponds to the initial amount of AgCl $C_{intial}$=10 mC.

(1) On a condition that AgCl replenishment is not performed, for the sensor usage lifetime of 16 days, the required length of the counter electrode is at least: $C_{16\ day}/C_{consume/day}$=20.8 mC/1.3 mC/day=16 mm.

(2) Therefore, on a condition that the replenishment method for the silver halide in the present application is not performed, the length of the counter electrode needs to exceed 16 mm in order to make the usage lifetime of the sensor achieve 16 days.

In this embodiment, on a condition that the replenishing technique for silver halide in the present invention is not used, the signal sensing section of the counter electrode needs to be configured with a relatively large size of Ag/AgCl material to achieve the usage lifetime of 16 days. Through the replenishment method for silver halide in the present invention, the replenishment step for silver halide is performed between two measurement steps. The consumption and replenishment of the silver halide cycles repeated in a short period of time (replenished when used), so the amount of Ag/AgCl material in the sensor can be reduced, and thereby the sensor is miniaturized. Therefore, there is no need to prepare 16 days of AgCl capacity for the signal sensing section material of the electrode for consumption. For example, the preparation of the capacity of AgCl for about 1-2 days can achieve a usage time of 16 days of the sensor. Thus, the present invention has the effect of prolonging the usage lifetime of the sensor. The capacity of AgCl for 1-2 days also refers to the initial amount of AgCl in the counter electrode before leaving the factory or before performing the first measurement. The initial amount of AgCl may be, for example, between about 1.3 and 2.6 mC, and can be in other smaller range or a larger range. In other embodiments, different AgCl capacities for 1-5 days, 1-3 days, 6-24 hours, and 6-12 hours can also be prepared. The size of the signal sensing section of the counter electrode can be configured in such a way that the counter electrode has a capacity which enables stable executions of each measurement step for glucose and the positive correlation between the measurement current and the glucose concentration in the body.

The prior art increased the electrode length/area to make the sensor reach the required measurement days without using the silver chloride replenishment technology of the present invention. For example, the length of the implantation end of the prior art is about 12 mm. Due to the long implantation length of the prior art, the implantation end needs to be implanted subcutaneous at an oblique angle to avoid the implantation end from implanting deeply into the subcutaneous tissue, which causes a large implantation wound. For another example, the capacity of AgCl for 1-2 days is about 1.3~2.6 mC, the length of the counter electrode for 1~2 days is 2.5~5 mm after conversion, and thus the length of the counter electrode needs 16 mm without using the replenishment method for silver halide in the present invention. Comparing to the example above, it is obvious that the present invention has more significant effect on shortening the size of the counter electrode. According to the silver chloride replenishment step of the present invention, the implantation end of the present invention can be shortened, for example, to no greater than 10 mm. Please refer to FIGS. 2A-2C, the lower half of the connecting area 117 to the second end 114 of the micro biosensor 100 of the present invention forms a short implantation end 118, as shown in FIGS. 2A and 2B. The implantation depth of the short implantation end 118 is at least a depth to the dermis where can measure the glucose concentration in the tissue fluid. According to the silver chloride replenishment step of the present invention, a length of the longest side of the short implantation end 118 is no greater than 6 mm, so that the short implantation end 118 of the micro biosensor 100 can be perpendicularly implanted under the biological epidermis. Preferably, the length of the longest side of the short implantation end 118 is no greater than 5 mm, 4.5 mm, 3.5 mm or 2.5 mm. The short implantation end 118 of the present invention includes the signal sensing section 132 of the counter electrode 130, and a length of the longest side of the signal sensing section 132 of the counter electrode 130 is no greater than 6 mm, preferably 2-6 mm, 2-5 mm, 2-4.5 mm, 2-3.5 mm, 0.5-2 mm or 0.2-1 mm.

Therefore, compared with the cases where the silver halide replenishment technique of the present invention is not used, the silver halide replenishment method of the present invention can effectively extend the micro sensor's usage lifetime, and can also greatly reduce the use of Ag/AgCl material on the counter electrode, which causes the size of the signal sensing section of the counter electrode to be reduced. Because of the reduced use of the Ag/AgCl material on the counter electrode, the sensor can be miniaturized and biological toxicity can be reduced. In addition, the reduced size of the electrode specifically refers to the shortened length of the implantation end of the sensor, which would reduce pain for the user during implantation.

While the invention has been described in terms of what is presently considered to be the most practical and preferred embodiments, it is to be understood that the invention need not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A method of measuring an analyte using a biosensor for prolonging a usage lifetime of the biosensor implanted subcutaneously to measure a physiological signal representative of a physiological parameter associated with the analyte in a biofluid, the biosensor comprising a working electrode and a counter electrode, the working electrode being at least partially covered by a chemical reagent configured to react with the analyte, the counter electrode having a silver and a silver halide, the method comprising the following cyclic steps of:
   a) performing a measurement step, including sub-steps of:
      i. applying a measurement potential difference across the working electrode and the counter electrode so that the working electrode has a higher voltage than that of the counter electrode during a measurement period, causing a first oxidation reaction to occur on the working electrode having an electrochemical reaction with the chemical reagent and the analyte, thereby the working electrode outputting a physiological signal, where the silver halide of the counter electrode has a consumption amount corresponding to the physiological signal; and
      ii. removing the measurement potential difference to stop the physiological signal measurement step, and converting the physiological signal to output a physiological parameter; and
   b) performing a replenishment step whenever the physiological parameter is obtained, including sub-steps of:
      i. applying a replenishment potential difference across the counter electrode and the working electrode during a replenishment period so that the counter electrode has a higher voltage than that of the working electrode, causing a second oxidation reaction to occur to the silver on the counter electrode, so that the silver chloride gains a replenishment amount, wherein the replenishment amount is related to the consumption amount that the silver halide of the counter electrode has an amount maintained in a safe storage range, and a next physiological signal and a next physiological parameter obtained in a next measurement step are kept in a stable correlation; and
      ii. removing the replenishment potential difference to stop the replenishment step.

2. The method according to claim 1, wherein the measurement potential difference and the replenishment potential difference are applied for a measurement time period and a replenishment time period respectively, and the measurement time period has a time value being one of a constant measurement time period value or a variable measurement time period value.

3. The method according to claim 2, wherein a total time period of the measurement time period plus the replenishment time period is a constant.

4. The method according to claim 2, wherein the replenishment potential difference has a constant voltage value, and the replenishment time period is dynamically adjusted based on the consumption amount of the silver halide.

5. The method according to claim 2, wherein the replenishment time period has a constant time period value, and the replenishment potential difference has a value dynamically adjusted based on the consumption amount of the silver halide.

6. The method according to claim 2, wherein the constant measurement time period is a time value being no greater than one selected from the group consisting of 15 seconds, 30 seconds, 1 minute, 2 minutes, 5 minutes and 10 minutes.

7. The method according to claim 1, wherein the amount of the silver chloride of the counter electrode in the safe storage range is maintained by controlling the replenishment amount to be close to or equal to the consumption amount.

8. The method according to claim 1, wherein the amount of the silver chloride of the counter electrode in the safe storage range is maintained by controlling the replenishment amount to be larger than the consumption amount.

9. The method according to claim 1, wherein the amount of the silver chloride of the counter electrode in the safe storage range is maintained by controlling the replenishment amount to be smaller than the consumption amount.

10. The method according to claim 1, wherein the amount of the silver chloride of the counter electrode in the safe storage range is maintained by controlling the replenishment amount to be unequal to the consumption amount.

11. A method of measuring an analyte using a biosensor for prolonging a usage lifetime of the biosensor implanted subcutaneously to measure a physiological signal representative of a physiological parameter associated with the analyte in a biofluid, the biosensor comprising a working electrode and a counter electrode, the working electrode being at least partially covered by a chemical reagent, the counter electrode including a silver and a silver halide having an initial amount, the method comprising cyclic steps of:
   applying a measurement voltage to drive the working electrode to measure the physiological signal, thereby obtaining the physiological parameter, where the silver halide is consumed by a specific amount; stopping applying the measurement voltage; and
   whenever the physiological parameter is obtained, applying a replenishment voltage to drive the counter electrode to cause an oxidation reaction, thereby the silver halide of a replenishment amount being replenished to the counter electrode, wherein a guarding value of a sum of the replenishment amount and the initial amount subtracting the consumption amount is controlled within a range of the initial amount plus or minus a specific value such that a next physiological signal and a next physiological parameter obtained are kept in a stable correlation.

12. The method according to claim 11, wherein the specific value is X, and the X satisfies a condition of: 0<X<the initial amount.

13. The method according to claim 11, wherein the measurement voltage is applied for a measurement time period, the replenishment voltage is applied for a replenishment time period, and the measurement time period has a time value being one of a constant measurement time period value and a variable measurement time period value.

14. The method according to claim 13, wherein the replenishment voltage has a constant voltage value, and the replenishment time period is dynamically adjusted based on the consumption amount of the silver halide.

15. The method according to claim 13, wherein the replenishment time period has a constant time value, and the replenishment voltage has a value dynamically adjusted based on the consumption amount of the silver halide.

16. The method according to claim 11, wherein the guarding value is secured by controlling the replenishment amount of the silver halide at one selected from the group consisting of being close to, equal to, larger than, smaller than, and unequal to the consumption amount of the silver halide to maintain an amount of the silver halide in a safe storage range.

17. A micro biosensor for subcutaneous implantation to measure a physiological parameter representative of a physiological signal associated with an analyte in a living body, comprising:
- a substrate;
- a chemical reagent;
- a working electrode disposed on the substrate, at least partially covered by the chemical reagent, and configured to be driven for a first oxidation reaction to measure the physiological signal for obtaining the physiological parameter within a measurement period;
- a counter electrode disposed on the substrate, and comprising a silver and a silver halide having an initial amount, the silver halide configured to be consumed by a specific amount within the measurement period; and
- a circuit configured to drive the counter electrode for a second oxidation reaction within a replenishment period whenever the respective physiological parameter is obtained, thereby replenishing a replenishment amount of the silver halide to the counter electrode,
- wherein the circuit is further configured to control a guarding value of a sum of the replenishment amount and the initial amount subtracting the consumption amount within a range of the original amount plus or minus a specific value such that a next physiological signal and a next physiological parameter obtained are kept in a stable correlation.

18. The micro biosensor according to claim 17, wherein the guarding value is controlled so that a ratio of an amount of the silver halide and a sum of an amount of the silver and the amount of the silver halide is larger than 0 and smaller than 1.

19. The micro biosensor according to claim 17, further comprising a short implantation end having a length no greater than 6 mm.

20. The micro biosensor according to claim 17, wherein the counter electrode is at least partially covered by the chemical reagent.

* * * * *